(12) United States Patent
Laughlin, II et al.

(10) Patent No.: US 10,267,796 B2
(45) Date of Patent: Apr. 23, 2019

(54) SCREENING METHODS OF MODULATING ADRENERGIC RECEPTOR GENE EXPRESSIONS IMPLICATED IN MELANOGENESIS

(75) Inventors: Leo Timothy Laughlin, II, Mason, OH (US); Tomohiro Hakozaki, Cincinnati, OH (US); Wenzhu Zhao, Mason, OH (US); Jiazhen Wang, Dayton, OH (US); John Crist Bierman, Colerain Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1591 days.

(21) Appl. No.: 13/278,465

(22) Filed: Oct. 21, 2011

(65) Prior Publication Data

US 2012/0197016 A1     Aug. 2, 2012

Related U.S. Application Data

(60) Provisional application No. 61/406,338, filed on Oct. 25, 2010.

(51) Int. Cl.
| | |
|---|---|
| *C12Q 1/02* | (2006.01) |
| *C07C 257/18* | (2006.01) |
| *C07C 233/51* | (2006.01) |
| *C07D 471/10* | (2006.01) |
| *C07D 405/14* | (2006.01) |
| *C07D 209/88* | (2006.01) |
| *C07D 459/00* | (2006.01) |

(Continued)

(52) U.S. Cl.
CPC ....... *G01N 33/566* (2013.01); *G01N 2500/10* (2013.01)

(58) Field of Classification Search
None
See application file for complete search history.

(56) References Cited

U.S. PATENT DOCUMENTS

| 5,462,856 A | 10/1995 | Lerner et al. |
| 6,051,386 A | 4/2000 | Lerner et al. |

(Continued)

OTHER PUBLICATIONS

M. Potenza, A Method for Evaluating the Effects of Ligands upon Gs Protein-Coupled Receptors Using a Recombinant Melanophore-Based Bioassay, Analytical Biochemistry, 1992, 206, pp. 315-322.*

(Continued)

*Primary Examiner* — Kathrien A Cruz
*Assistant Examiner* — Andrew P Lee
(74) *Attorney, Agent, or Firm* — John G. Powell

(57) ABSTRACT

Embodiments of screening methods for determining test agents effective for modifying the appearance of pigmented skin are provided. The screening method may comprise the steps of contacting a cell, a cell culture, or bulk cells with the test agent, wherein the cell, the cell culture, or the bulk cells comprise ADRβ1 receptors, and determining based on the binding interaction of the test agent with the ADRβ1 receptors whether the test agent is an effective ADRβ1 receptor antagonist suitable for modifying the appearance of pigmented skin, wherein a test agent is considered to be an effective ADRβ1 receptor antagonist when it defines a half maximal inhibitory concentration of less than about 1000 ppm.

9 Claims, 8 Drawing Sheets

(51) Int. Cl.
  *G01N 21/64* (2006.01)
  *C07C 229/52* (2006.01)
  *G01N 33/566* (2006.01)

(56) References Cited

U.S. PATENT DOCUMENTS

| | | | |
|---|---|---|---|
| 6,376,513 B1* | 4/2002 | Akahane | A61K 31/00 514/312 |
| 6,974,799 B2 | 12/2005 | Lintner | |
| 7,354,926 B2 | 4/2008 | Lintner | |
| 2004/0072287 A1* | 4/2004 | Tan et al. | 435/69.1 |
| 2006/0013782 A1* | 1/2006 | Mahalingam et al. | 424/61 |
| 2006/0074097 A1* | 4/2006 | Bissett | A61K 31/155 514/275 |
| 2007/0202180 A1* | 8/2007 | Liversidge | A61K 9/145 424/489 |
| 2011/0071049 A1* | 3/2011 | Heintz et al. | 506/9 |

OTHER PUBLICATIONS

U. Mullins, Melatonin Agonists Induce Phosphoinositide Hydrolysis in Xenopus Laevis Melanophores, Celullar Signalling, 1997, 9(2), pp. 169-173.*

E. Yang, Norepinephrine upregulates VEGF, IL-8, and IL-6 expression in human melanoma tumor cell lines: Implications for stress-related enhancement of tumor progression, Brain, Behavior, and Immunity, Feb. 2009, 23, pp. 267-275.*

Potenza, A Method for Evaluating the Effects of Ligands upon Gs Protein-Coupled Receptors Using a Recombinant Melanophore-Based Bioassay, Analytical Biochemistry, 1992, 206, pp. 315-322.*

Yang, Norepinephrine upregulates VEGF, IL-8, and IL-6 expression in human melanoma tumor cell lines: Implications for stress-related enhancement of tumor progression, Brain, Behavior, and Immunity, Feb. 2009, 23, pp. 267-275.*

Mullins, Melatonin Agonists Induce Phosphoinositide Hydrolysis in Xenopus Laevis Melanophores, Cellular Signalling, 1997, 9(2), pp. 169-173.*

Gillbro, The melanogenesis and mechanisms of skin-lightening agents—existing and new approaches, International Journal of Cosmetic Science, 2011, 33, pp. 210-222.*

European Patent Office PCT Partial International Search dated Feb. 23, 2012 in reference to co-pending PCT/US2011/057608 filed Oct. 25, 2011.

Raja K Sivamani et al.; An Epinephrine-Dependent Mechanism for the Control of UV-Induced Pigmentation; Journal of Investigative Dermatology; Aug. 21, 2008; pp. 784-787; vol. 129, No. 3.

Serget A. Grando et al.; Adrenergic and Cholinergic Control in the Biology of Epidermis: Physiological and Clinical Significance; Journal of Investigative Dermatology; Sep. 1, 2006; pp. 1948-1965; vol. 126, No. 9.

International Search Report and Written Opinion of the International Searching Authority PCT/US2011/057608 dated Apr. 27, 2012, 19 pages.

Katayama et al., Subtypes of β-adrenoceptos in the melanophore of *Oryzias latipes* (Teleostei), Bull. Fac. Life Env. Sci. Shimane Univ., 1:7-15 (1996).

U.S. Appl. No. 07/555,724, filed Jul. 19, 1990, Michael R. Lerner et al.

* cited by examiner

SCREENING METHODS OF MODULATING ADRENERGIC RECEPTOR GENE EXPRESSIONS IMPLICATED IN MELANOGENESIS

CROSS-REFERENCE TO RELATED APPLICATIONS

This application claims priority to U.S. Provisional Application Ser. No. 61/406,338 filed Oct. 25, 2010, which is incorporated by reference herein in its entirety

TECHNICAL FIELD

The present invention relates to gene panels and genomic transcriptional profiling-derived biomarkers and also relates to methods for determining and evaluating agents which transcriptionally regulate genes, specifically adrenergic receptor genes, implicated in melanin synthesis (melanogenesis) and regulation of age spots in human skin.

BACKGROUND

Skin aging is a multifactorial process driven by both intrinsic factors (e.g., effects of natural course of chronological aging) and extrinsic factors (e.g., environmental toxins/pollutants and smoking).

The skin comprises, in particular, keratinocytes, melanocytes and nerve cells, fibroblasts, Langerhans cells, endothelial cells, smooth muscle cells, etc. Referring to FIG. 1, the keratinocytes and melanocytes are present in the epidermis. The melanocytes are located in the basal layer of the epidermis, and they constitute the site for melanogenesis. Due to their close contact with the keratinocytes, the melanocytes transfer to the keratinocytes the newly synthesized melanin in the form of melanosomes, thereby giving the skin its coloration. While melanocytes actually produce the pigment response, keratinocytes produce epinephrine, a catecholamine which is reported to trigger the melanocyte to produce pigment. This triggering of melanin via catecholamines, such as epinephrine, is called catecholamine biosynthesis, which will be described below. Thus, these two cell types work together symbiotically to modulate pigmentation. The type and the amount of melanin distributed in the keratinocytes determine the primary coloration of the skin.

Referring to FIG. 2, melanogenesis, or melanin synthesis, is a biological phenomenon initiated by hydroxylation of the L-tyrosine amino acid resulting from the formation of L-dihydroxyphenyl-alanine (L-DOPA), which is in turn converted to DOPA-chrome by the action of a specific melanocyte-associated enzyme, tyrosinase. Consecutive reduction and oxidation reactions result in the conversion of the DOPA-chrome to melanin. The production of tyrosinase and its activity determine in part the amount of melanin produced. The amount and the type of melanin transferred to the keratinocytes determine, for their part, the degree of visual pigmentation of human skin.

Skin aging or the appearance of skin aging is a function of melanogenesis. Skin aging or age spots are perceived as a contrast in skin tone. As used herein, "age spot" generally refers to spots on the skin associated with aging, and may encompass solar lentigo, freckles, melasma, seborrheic keratoses, post inflammatory hyperpigmentation, etc. As used herein, "tone" generally refers to the visual perception of a smooth and evenly-pigmented surface. Skin aging affects texture and pigmentation, creating contrasts on the face that may be a result of shadows caused by wrinkles or color changes caused by age spots. In young skin, melanin is evenly distributed, and melanocyte activity is low, restricted to the production of constitutive pigmentation only. UV radiation in sunlight transiently activates melanocytes to produce melanin that is evenly distributed, as in a tan. In aging skin, some melanocytes may be damaged by cumulative UV exposure, causing them to be permanently "switched on" and overproduce melanin. This overzealous melanogenesis production can eventually create permanent local discoloration with sufficient size and contrast to appear as age spots (lentigines) or as diffuse hyperpigmentation. As skin turnover decreases with age, microscopic bits of melanin ("melanin dust") can become trapped in the epidermis and stratum corneum, contributing to a duller appearance. Uneven distribution of melanin manifests itself as age spots and hyperpigmentation. Hyperpigmentation in the age spot tissue relates to one or more of the following known factors: higher activity of tyrosinase, an above described melanocyte enzyme, and a higher instance of matured melanosomes and a higher retention rate of melanin/melanosomes in melanocytes or keratinocytes after they are synthesized.

Generally, UV radiation induced hyperpigmentation is thought to partially contribute to the actions of propiomelanocortin-derived peptides and a melanocyte stimulating hormone on the melanocyte melanocortin-1 receptor by increasing intracellular cAMP. Studies in propiomelanocortin-deficient mice and in animals with nonfunctional melanocortin-1 receptors reveals that they are still able to produce melanin in response to forskolin suggesting that alternate cAMP dependent pathways also induce melanogenesis.

One such alternate cAMP-dependent pathway involves the adrenergic receptors, which are pharmacologically divided into two groups: α and β. The adrenergic receptors are a prototypic family of guanine nucleotide binding regulatory protein-coupled receptors that mediate the physiological effects of the hormone epinephrine and the neurotransmitter norepinephrine. There are 3 types of beta adrenergic receptors: ADRβ1, ADRβ2 and ADRβ3, subtyped on the basis of differential pharmacological response to catecholamines and specific antagonists as well as differences in protein sequence. Moreover, there are multiple subtypes of alpha adrenergic receptors: ADRα1A, ADRα1B, ADRα1D, ADRα2A, ADRα2B, and ADRα2C.

According to Schallreuter, K. U. et al., *The induction of the α-1-adrenoreceptor signal transduction system on human melanocytes*, Experimental Dermatology 1996; Vol. 5, Issue 1, pages 20-23, human melanocytes do not express α1, β1 or β2 adrenoreceptors without extracellular stimulation. Introduction of norepinephrine causes a time-dependent induction of α1 receptors; however, there is no effect on melanogenesis. In contrast β-adrenergic receptors in melanocytes were not induced by norepinephrine stimulation, thus norepinephrine synthesized by the melanocyte does not appear to mediate pigmentation/melanogenesis.

In contrast, induction of catecholamine biosynthesis in keratinocytes correlates with an increase in ADRβ2 receptors. Schallreuter conducted studies which implicated ADRβ2 signaling pathways and catecholamine synthetic networks within the epidermis. Both keratinocytes and melanocytes express ADRβ2 and both cell types have the enzymatic machinery for catecholamine biosynthesis, specifically norepinephrine synthesis, although only keratinocytes are known to synthesize epinephrine. The secretion of epinephrine from the keratinocytes stimulates the beta adrenergic receptors on the melanocytes, which increases intracellular cAMP, and thereby increases melanogenesis.

Sivamani et al., *An Epinephrine-Dependent Mechanism for the Control of UV-Induced Pigmentation,* Journal of Investigative Dermatology (2009), vol. 129, pages 784-786 disclosed that keratinocytes secrete epinephrine in response to UV radiation, and the epinephrine stimulates the beta adrenergic receptors on melanocytes to increase melanin synthesis. Thus, Sivamani established a link between stress, UV radiation, and pigmentation. Additionally, Sivamani confirmed the general consensus also provided in Schallreuter that α1 receptors have no effect on melanogenesis.

Grando, *Adrenergic and Cholinergic Control in the Biology of Epidermis: Physiological and Clinical Significance,* Journal of Investigative Dermatology Vol. 126, pages 1948-1965 (2006) teaches the epidermal adrenergic signal controls calcium homeostasis, and suggests that pigmentation may be controlled via the β2 and α1 adrenergic receptors; however, Grando's examples centered on the relationship of ADRβ2 to melanogenesis. Grando further asserts that melanocytes express only ADRβ2 receptors, whereas ADRβ1 receptors are considered absent.

A greater understanding of the biochemical processes responsible for aging, such as the mechanism described above, has invigorated the cosmetics industry and resulted in the emergence of a new class of cosmetic actives sometimes referred to as "cosmeceuticals." The purported effects, including but not limited to antioxidant, anti-inflammatory and free-radical-scavenging effects, derive from the underpinning science.

The present inventors recognized the deficiencies associated with evaluation of known cosmetic agents for cosmetically functional effects and the deficiencies associated with the identification of agents that actually achieve a theoretically-based effect to provide actual, verifiable anti-aging benefit to skin. Accordingly, the present inventors recognized a continual need for reliable and efficient in-vitro methods to identify agents effective in reducing the size and intensity of age-related skin spots, specifically by modulating the production of melanin. While the literature has established a link between ADRβ2 receptors and melanogenesis generally, the linkage between adrenergic receptors and melanogenesis in age spots is not well established, and there is still a need to identify additional adrenergic receptors which modulate melanogenesis in age spots.

SUMMARY

Embodiments of the present invention are directed to applying the technologies of genomics and proteomics to develop agents that modulate melanin production to reduce age spots and improve skin tone. Global gene expression profiling provides a useful means to identify key aspects of the skin aging process and provides information permitting the development of the present inventive skin technologies. An important aspect of skin aging that can be addressed by application of genomics and proteomics is the reduction of aging spots or hyperpigmentation in the skin. Using this transcriptional analysis approach, it is possible to detect the effect on melanin synthesis in response to the compounds. Gene microarrays are new tools for understanding changes occurring at the transcriptional level during skin aging. The present inventors gathered gene expression data and applied advanced bioinformatics to identify particular pathways affected by aging.

Specifically, the present inventors, by utilizing modern genomics analysis and siRNA knockdown technologies as described below, found a linkage between ADRβ1 receptors and ADRβ3 receptors and melanogenesis, and further recognized that modulating ADRβ1 receptors and ADRβ3 receptors controls the production of melanin in age spots. To demonstrate this linkage, genomic analysis of age spots provided below shows a significant overexpression of ADRβ1 genes in age spots compared to non-involved skin. In contrast, while ADRβ1 genes demonstrate a much greater expression in age spots compared to non-involved skin, transcripts from genes normally associated with the melanin synthesis, such as tyrosinase, and tyrosinase-related protein 1, do not demonstrate any significant change in expression level in age spots versus non-involved skin.

Based on these inventive discoveries, a screening method for determining at least one test agent effective for modifying the appearance of pigmented skin is provided. The method comprises contacting a cell, a cell culture, or bulk cells with the test agent, wherein the cell, the cell culture, or the bulk cells comprise ADRβ1 receptors, and determining based on the binding interaction of the test agent with the ADRβ1 receptors whether the test agent is an effective ADRβ1 receptor antagonist suitable for modifying the appearance of pigmented skin, wherein a test agent is considered to be an effective ADRβ1 receptor antagonist when it defines a half maximal inhibitory concentration of less than about 1000 ppm.

In accordance with further embodiments, another screening method for determining at least one test agent as effective for modifying the appearance of pigmented skin is provided. The method comprises contacting a cell, a cell culture, or bulk cells with the test agent, wherein the cell, the cell culture, or the bulk cells comprise ADRβ3 receptors, and determining based on the binding interaction of the test agent with the ADRβ3 receptors whether the test agent is an ADRβ3 receptor agonist suitable for modifying the appearance of pigmented skin.

In accordance with other embodiments, additional screening methods are directed to determining test agents effective as ADRα1B receptor antagonists or ADRα2C receptor antagonists suitable for modifying the appearance of pigmented skin.

Further embodiments relate to cosmetic agents that incorporate these agents which modulate the production of melanin in human skin.

Features and benefits of the various embodiments of the present invention will become apparent from the following description, which includes figures and examples of specific embodiments intended to give a broad representation of the invention. Various modifications will be apparent to those skilled in the art from this description and from practice of the invention. The scope is not intended to be limited to the particular forms disclosed and the invention covers all modifications, equivalents and alternatives falling within the spirit and scope of the invention as defined by the claims.

BRIEF DESCRIPTION OF THE DRAWINGS

The following detailed description of specific embodiments of the present disclosure can be best understood when read in conjunction with the following drawings.

DETAILED DESCRIPTION

Embodiments of the present invention relate to minimizing the production of age spots by modulating adrenergic receptors, specifically beta adrenergic receptors, such as ADRβ1 and ADRβ3 and alpha adrenergic receptors, such as ADRα2C and ADRα1B.

For beta adrenergic receptors, a review of signal transduction pathways indicate that ADRβ1 and ADRβ2 receptors share similar transduction pathways that lead to increased intracellular cAMP production which ultimately leads to stimulation of tyrosinase expression. This signal transduction pathway intersects the signal transduction pathway of melanocortin 1 receptor (MC1R), a known pro-pigmentation pathway as shown in FIG. 3.

Figure 1:
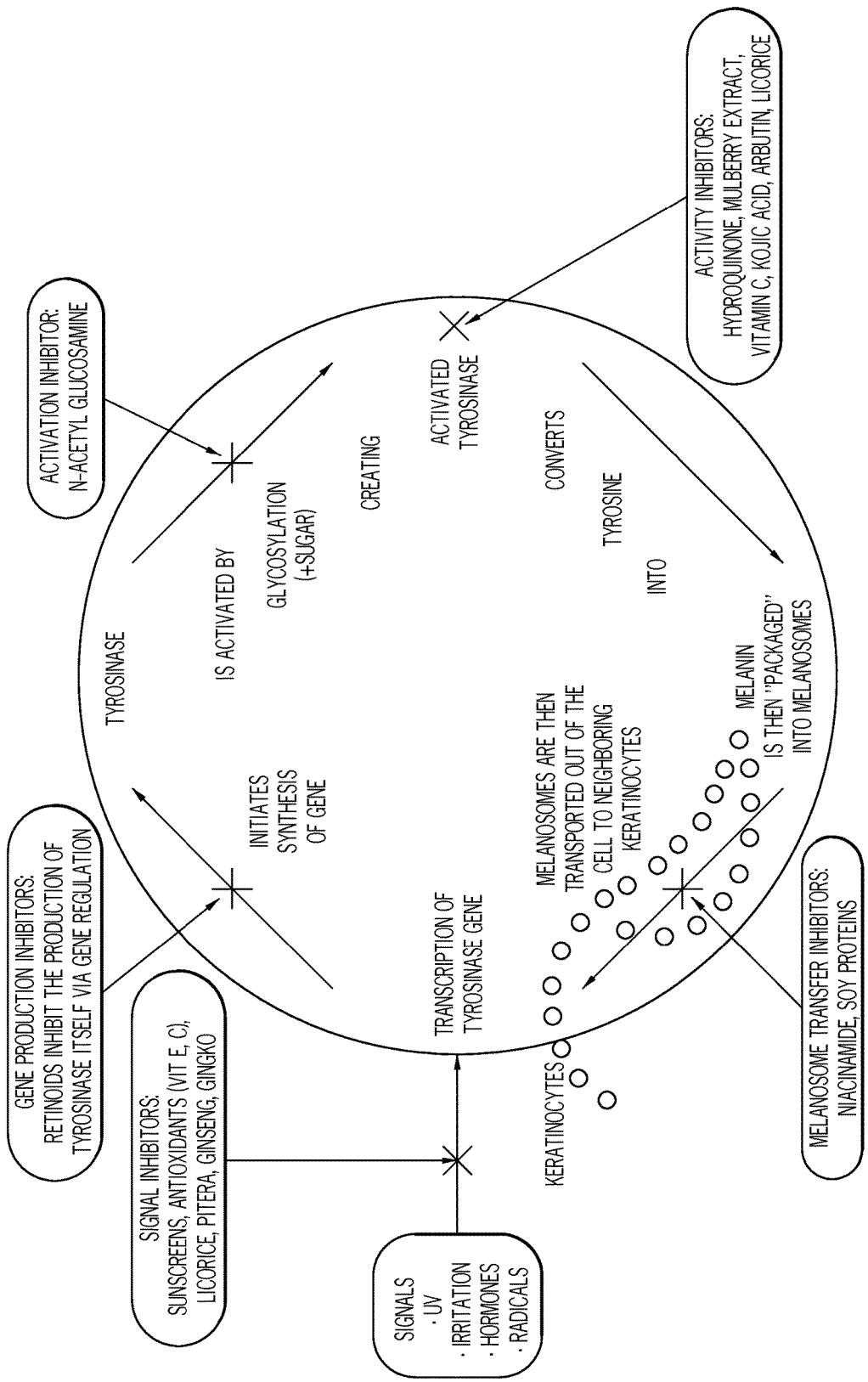
FIG. 1 is a schematic view of a melanin synthesis pathway.
Figure 2:
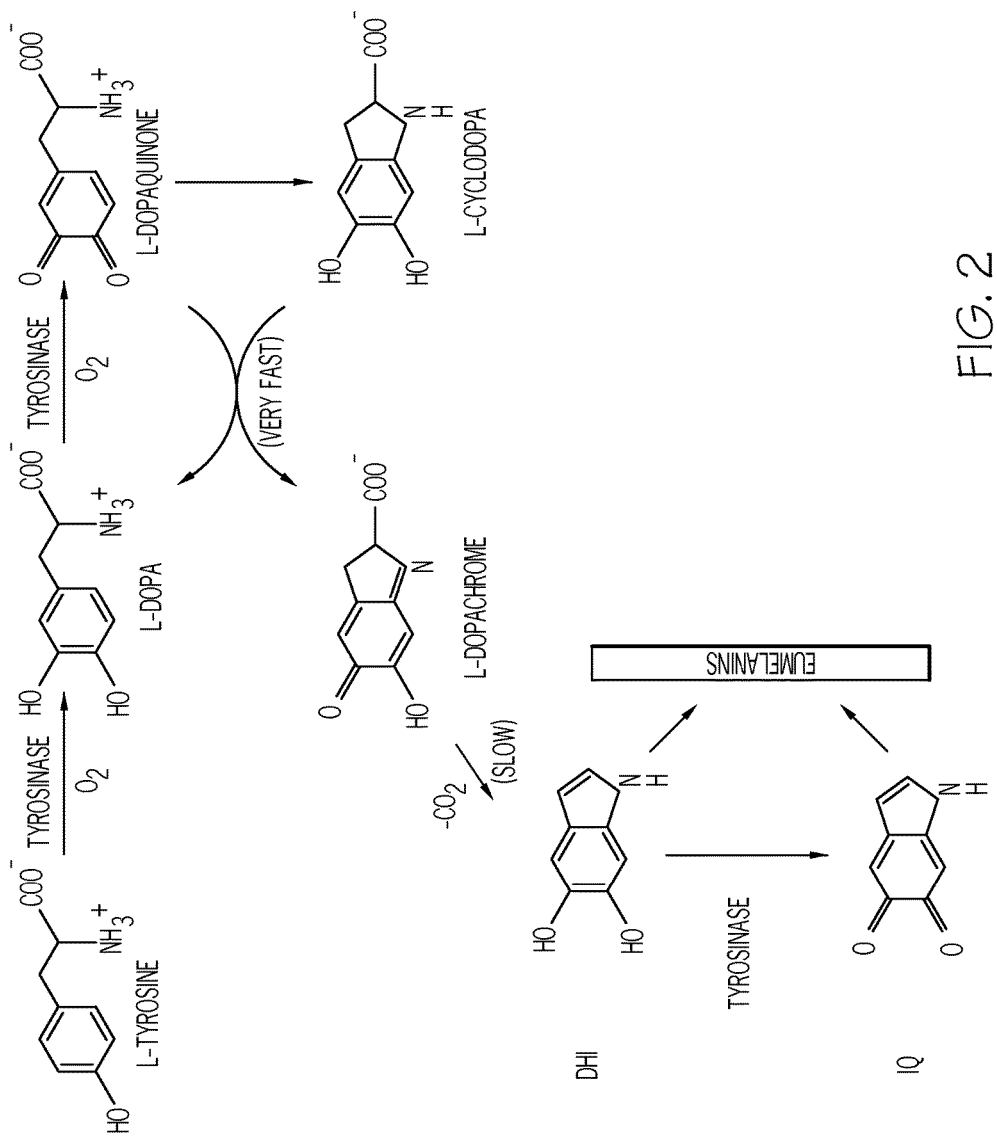
FIG. 2 is another schematic view of a melanin synthesis pathway.
Figure 3:
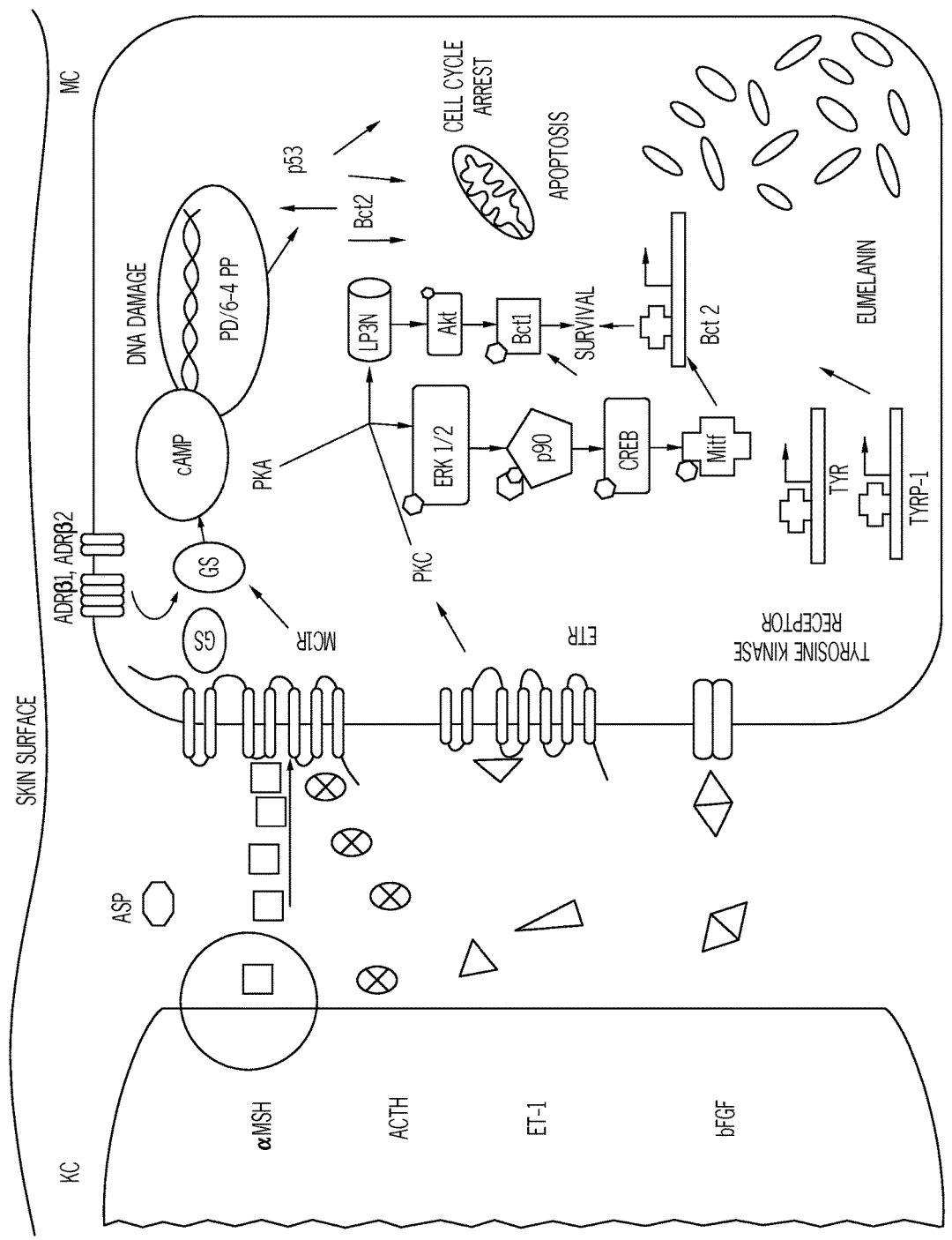
FIG. 3 is a schematic view depicting the intersection of a melanin synthesis pathway by ADRβ1 and ADRβ2 receptors.

As stated above and as depicted in FIG. 3, triggering of ADRβ1 and ADRβ2 receptors results in elevated cAMP levels, which drive tyrosinase production, thus intersecting known pathways to drive pigmentation. Specifically, as shown, the ADRβ1 and ADRβ2 receptors intersect the Gs G protein, which activates adenylyl cyclase, catalyzing the formation of cyclic adenosine monophosphate (cAMP). Increased levels of cAMP stimulate increased expression of microphthalmia-associated transcription factor (MITF), which proceeds downstream to tyrosinase upregulation. MITF helps control the development and function of the melanocytes (i.e., controls the level of melanin produced in the skin).

Since ADRβ1 and ADRβ2 receptors share similar pigmentation pathways, it would be expected that both ADRβ1 and ADRβ2 genes would be overexpressed in age spots which have an excess of melanin; however, this is not the case. Via genomics studies, the present inventors surprisingly found that that the ADRβ1 gene is highly upregulated in age spots, whereas the ADRβ2 gene is not highly upregulated in age spots. As used herein, highly upregulated means that the genes demonstrated a fold change value of at least 2 and a p-value of less than 0.05 in the age spots.

Referring to Table 2 below, the present inventors conducted a comparative experimental genomics study using Affy chips on biopsied skin samples with age spots and without age spots (i.e. non-involved skin). The genomics study utilized a microarray, a technology widely used in molecular biology and genomic studies. A microarray comprises an arrayed series of nucleic acid oligonucleotides, each containing a probe for a target gene. A probe is a short section of a target gene (or other target DNA) that is designed to hybridize to a target cDNA or cRNA sample. The hybridization is thereafter detected and quantified by methods well-known in the art, which may include fluorophore-labeled targets, to determine relative abundance of the specific sequence in the sample. An array may contain thousands of probes, and a "global" array is understood to contain a probe for an entire population of known genes in a species. Generally the probes are attached via a linking chemistry to a solid substrate such as a glass or silicon chip. Colloquially, these are known as Affy chips when an Affymetrix™ brand chip is employed. Such microarrays are also known as gene chips. Many other microarray platforms or detection systems are contemplated herein. One embodiment of the invention contemplates a unique assembly of hybridizing oligonucleotides targeting a unique panel of genes, however, which permits, inter alia, practice of the methods of the invention.

Upon statistically analyzing the biopsied skin samples obtained in the study, the ADRβ1 gene was found to be significantly upregulated in age spots (e.g., solar lentigo) as compared to uninvolved skin as demonstrated by a fold change of 14.5 for age spots versus uninvolved skin. Meanwhile, the expression levels of ADRβ2 and ADRβ3 are not significantly different in age spots compared to uninvolved skin.

TABLE 1

| Gene | Fold Change | P-value |
|---|---|---|
| ADRβ1 | 14.51 | 0.0441 |
| ADRβ2 | 0.9 | 0.2952 |
| ADRβ3 | 4.7 | 0.9664 |

Based on these discoveries, the present invention is directed to gene panels comprising genes correlating to the production and modulation of melanin in human skin. The gene panel comprises the ADRβ1 gene and optionally the ADRβ2 gene. In specific embodiments, the gene panel may comprise both the ADRβ1 gene and the ADRβ2 gene. These receptor genes are present in both the melanocytes and keratinocytes.

The amount and activation of these genes and the receptors encoded in the gene panel correlate to the amount of melanin present in hyperpigmented spots, freckles, melasma, solar lentigo, or combinations thereof. Specifically, these genes facilitate the synthesis of melanin when encoded into receptor proteins. In further embodiments, the present invention may also be directed to a biomarker panel comprising one or more gene products (i.e., the receptor proteins) of the genes of the present gene panels. The one or more gene products may comprise ADRβ1 receptor proteins and optionally ADRβ2 receptor proteins. In further embodiments, the one or more gene products may comprise ADRβ1 receptor proteins and ADRβ2 receptor proteins. To isolate agents which bind to the ADRβ1 gene and the encoded products therefrom, a microarray comprising immobilized oligonucleotides which hybridize specifically to nucleic acids is utilized.

Utilizing these microarrays, the present invention is further directed to screening methods for determining whether an agent is effective for improving the appearance of pigmented skin. The method may comprise contacting a cell, a cell culture, or bulk cells with a test agent, wherein the cell, the cell culture, or the bulk cells comprise ADRβ1 receptors. The test agent is some composition which binds or hybridizes to a specific nucleic acid. Various oligonucleotide compositions are contemplated as suitable for the test agent.

In one embodiment, the test agent is a palmitoylated peptide. In a further embodiment, the test agent is selected from the group consisting of palGQPR, palGHK, acetylGHK, acetyl-GQPR, hexamidine, undecylenoyl phenylalanine, and combinations thereof.

The method further comprises determining whether test agents are effective for improving the appearance of pigmented skin if the test agent is an antagonist of the ADRβ1 receptors. In one embodiment, the test agent may be identified as an ADRβ1 receptor antagonist if the test agent defines a half maximal inhibitory concentration (IC50) of less than about 1000 ppm. In further embodiments, the ADRβ1 receptor antagonist defines a half maximal inhibitory concentration of less than about 100 ppm, or less than about 50 ppm. By utilizing this metric of maximal inhibitory concentration, it is possible to correlate the antagonistic activity of the ADRβ1 receptor antagonists with an ability of the ADRβ1 receptor antagonists to improve the appearance of hyper-pigmented spots in human skin. In further embodiments, when the ADRβ1 receptor antagonists bind to the ADRβ1 receptors, a luminescent reference signal may be generated, which may be measured by a luminometer, a fluorescence plate reader, or a fluorometer.

As shown below in Table 2, the present inventors have further recognized that modifying a test agent from a peptide to a palmitoylated peptide greatly improves its efficacy as an ADRβ1 inhibitor. For example, the potency of GHK and GQPR peptides are greatly improved when comparing unmodified GHK and GQPR to palmitoylated GHK and GQPR. Further as shown in Table 2, modifying unmodified GHK and GQPR to produce acetylGHK and acetylGQPR also improve the efficacy as ADRβ1 inhibitor, thus it is contemplated that other peptide modifications may also prove beneficial for ADRβ1 receptor inhibition.

TABLE 2

| Peptide | ADRβ1 IC 50 (ppm) |
| --- | --- |
| palGQPR | 0.23 |
| palGHK | 3.3 |
| AcetylGHK | 45 |
| AcetylGQPR | 45 |
| GHK | 1100 |
| GQPR | 1200 |

While the method is directed to screening for ADRβ1 receptor antagonists, it is contemplated that the testing agents may also act as antagonists of the ADRβ2 receptors. In detecting for antagonists of the ADRβ2 receptors, additional cells, cell cultures or bulk cells may be utilized. The method may further comprise contacting a second cell, a second cell culture, or a second set of bulk cells with the test agent and determining whether the test agent is effective for improving the appearance of pigmented skin if the test agent is an antagonist of the ADRβ2 receptors. As ADRβ1 and ADRβ2 have a similar transduction pathway, the siRNA work in B16 cells implicates both ADRβ1 and ADRβ2 as being pro-pigmenting receptors functionally; however, the expression profile in age spots surprisingly distinguishes ADRβ1 from ADRβ2 in regulation, because ADRβ1 is significantly upregulated in age spots.

In further embodiments, the antagonists for the ADRβ1 receptor and/or ADRβ2 receptor may be incorporated into a cosmetic composition formulated for topical application to skin. This cosmetic composition, which may comprise various additional ingredients familiar to one of ordinary skill in the art, utilizes these ADRβ1 receptor and/or ADRβ2 receptor antagonists to improve the pigmented appearance of the skin.

Determining test agents suitable as ADRβ1 antagonists, ADRβ2 antagonists, or combinations thereof may utilize a melanin synthesis assay selected from the group consisting of a B16 cell assay or a skin model. The B16-F1 cells, which are murine melanoma cells obtained from American Tissue Culture Collection (ATCC), contain the synthetic machinery for melanin production and respond to some benchmark whitening/tanning agents. The following experiment depicts one exemplary method of determining the effect of test agents on melanin synthesis.

B16 Cell Assay Experiment

In the experiment, 0.5 mL of B16-F1 cells are added to 29.5 ml of B16-F1 culture media to 2 separate T-150 flasks, and grown to near (~80%) confluency. The culture media B16-F1 comprises the following components as shown in Table 1 below:

TABLE 3

| Culture Media Component |
| --- |
| 500 mL DMEM 500 mL DMEM (Dulbecco's Modification of Eagle's Medium) |
| 50 mL FBS (Fetal Bovine Serum) |
| 5 mL Pen/Strep (Penicillin/Streptomycin) |

The cells from the T-150 flasks were trypsinized and counted with a hemacytometer. Then, cell vials ($1 \times 10^6$ cell aliquots) were frozen in a mixture comprising 95% B16-F1 culture medium and 5% DMSO (Dimethyl sulfoxide) and placed in liquid Nitrogen. All cell culture reagents (except trypsin) were heated in a 37° C. water bath.

On day zero, 29 mL of B16-F1 culture media was placed into a T-150 flask at 37° C. Then, a vial of the frozen cells was obtained, thawed in a 37° C. water bath, and placed in the T-150 flask. The flask was agitated to mix the cells with the media, and then the flask was incubated for 3 days at 37° C. in a humidified environment comprising 5% $CO_2$. On day 3, the cells from the flask were trypsinized and the cell density was determined. At which point, the cells were split into a 96-well plate with 2,500 cells per well. At day 5, the cells were treated with the test agents. On day 7, the cells were assayed for melanin production and toxicity.

Figure 4:
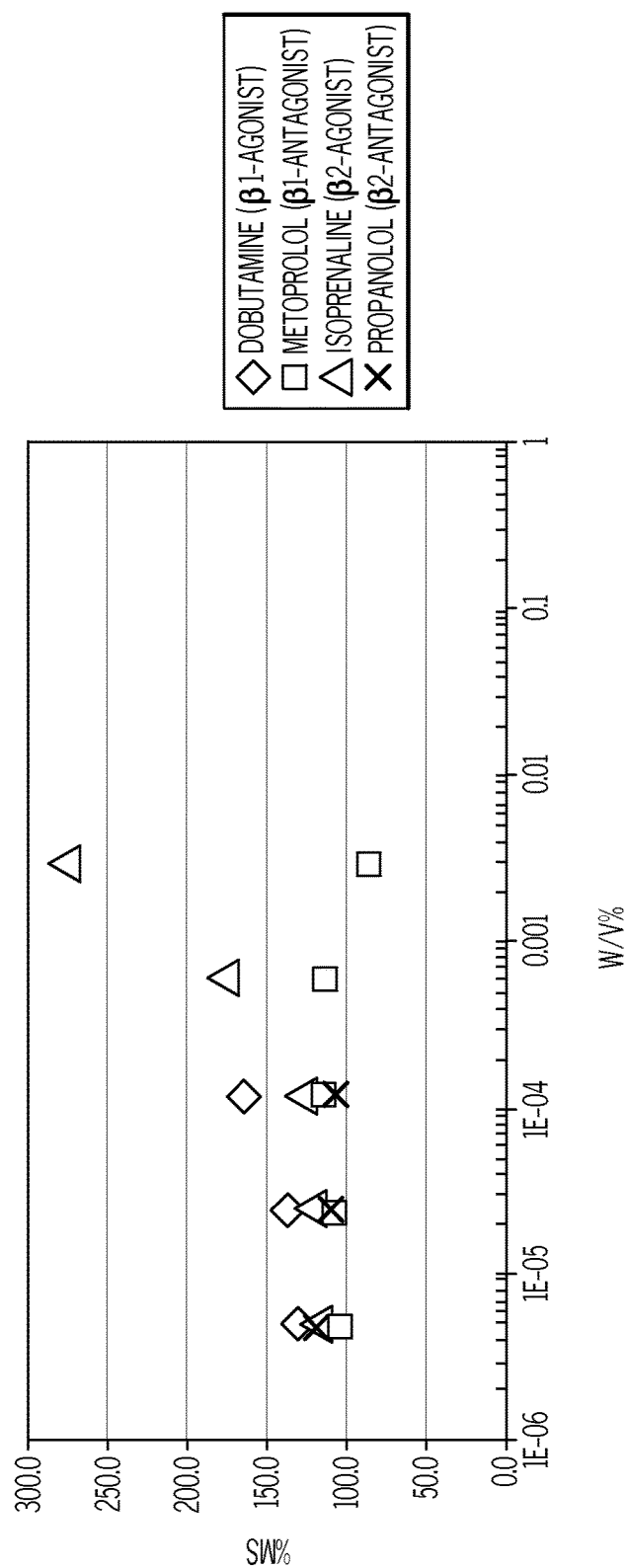
FIG. 4 is a graphical illustration depicting the effect of ADRβ1 and ADRβ2 receptor agonists and antagonists on melanin synthesis.
Figure 5:
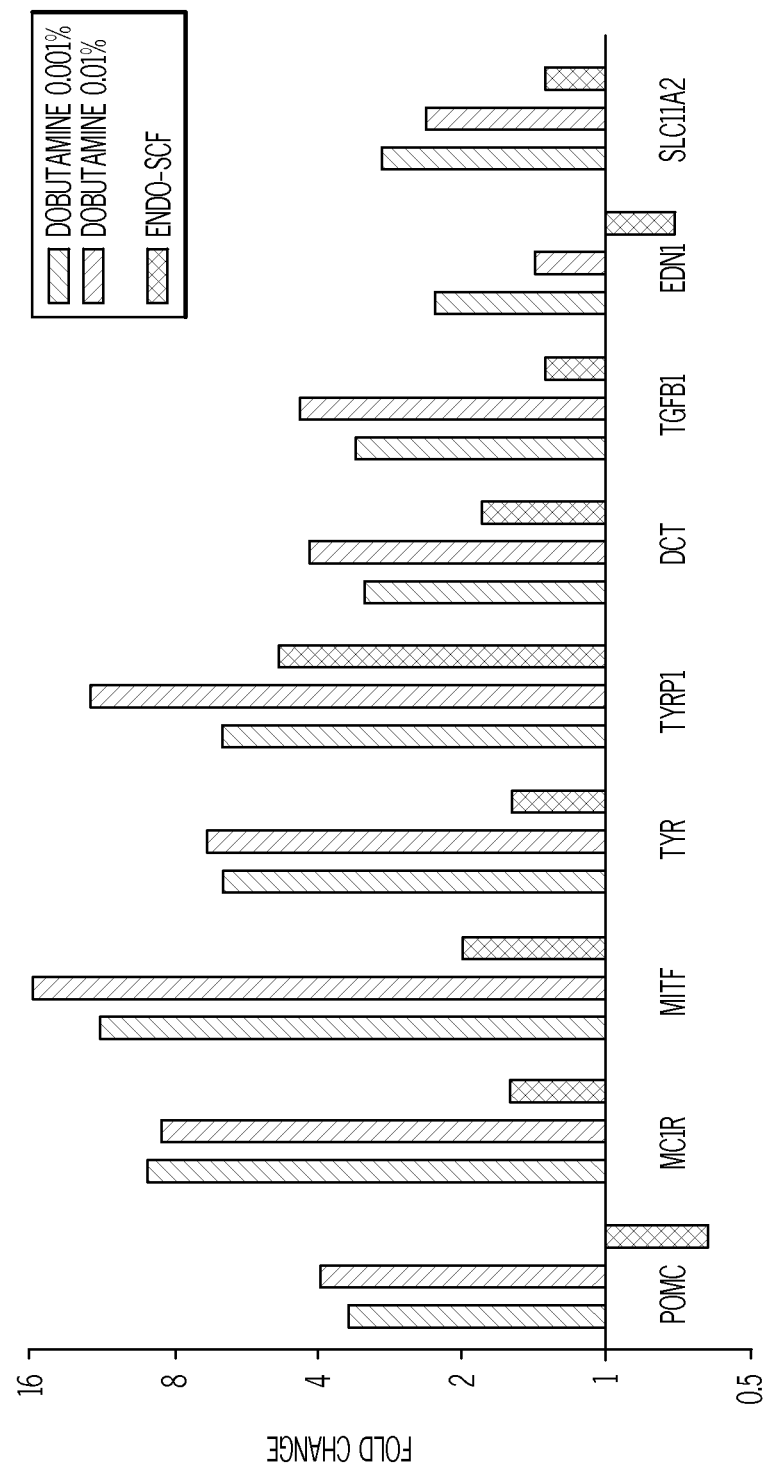
FIG. 5 is a graphical illustration depicting the effect of dobutamine on human skin explants.

Referring to the graphical illustration of FIG. 4, the present inventors utilized the B 16 cell assay to demonstrate the effect of known ADRβ1 and ADRβ2 agonists and antagonists. As shown, increasing the concentration (w/v %) of known ADRβ1 agonist dobutamine and known ADRβ2 agonist isoprenaline increases the melanin synthesis (% MS or % melanin synthesis). In the case of the isoprenaline ADRβ2 agonist, the melanin synthesis was greatly improved to almost 300% as the concentration of isoprenaline increased. As stated above, ADRβ1 and ADRβ2 stimulation result in elevated cAMP levels which drive tyrosinase production in known melanogenesis pathways. Moreover, referring to FIG. 5, the inventors determined that dobutamine, an ADRβ1 agonist, induces pigmentation gene expression in human skin explants more than the paracrine factors Stem Cell Factor & Endothelin (Endo-SCF), which are also associated with Age Spots.

In addition to recognizing that antagonists of ADRβ1 and/or ADRβ2 receptors are effective at controlling the appearance of human skin by modulating melanogenesis, the present inventors have also recognized that agonists of ADRβ3 also aid in controlling the appearance of human skin by modulating melanogenesis. In contrast to ADRβ1 and ADRβ2 receptors, ADRβ3 receptors were found by the present inventors to have different downstream signal transduction pathways, and thus a different relationship to melanogenesis.

ADRβ3 receptors stimulate nitric oxide production through the activation of endothelial nitric oxide synthase. Nitric oxide activates guanylate cyclase and increases cyclic guanosine monophosphate (cGMP) levels, and reduces cAMP levels. By reducing cAMP levels, tyrosinase production is reduced. As tyrosinase is a key component of pigmentation pathways, reducing tyrosinase reduces melanin production and thereby reduces age spots.

Consequently, further embodiments of the present invention are directed to a gene panel comprising the ADRβ3 gene and optionally at least one of the ADRβ1 genes and the ADRβ2 genes. In addition to the gene panel, the present invention may encompass biomarker panels comprising one or more encoded gene products comprising ADRβ3 receptor proteins and optionally at least one of the ADRβ1 and ADRβ2 receptor proteins.

Noting the efficacy of ADRβ3 receptor agonists, embodiments of the present invention are directed to screening methods for determining agents effective as ADRβ3 receptor agonists. The method may comprise contacting a cell, a cell culture, or bulk cells with a test agent, wherein the cell, the cell culture, or the bulk cells comprise ADRβ3 receptors, and determining test agents effective for improving the appearance of pigmented skin if the test agent is an agonist of the ADRβ3 receptors.

Like the above described cosmetic compositions or products, the agonists for the ADRβ3 receptor may be incorporated into a cosmetic composition formulated for topical application to skin. To further control the production of melanin, the cosmetic composition may include ADRβ1 receptor antagonists, ADRβ2 receptor antagonists, or both. This cosmetic composition, which may comprise various additional ingredients familiar to one of ordinary skill in the art, may utilize these ADRβ3 receptor agonists, alone or in combination with the ADRβ1 receptor and/or ADRβ2 receptor antagonists to improve the pigmented appearance of the skin. The combination of ADRβ1 antagonists with ADRβ3 agonists is believed to work synergistically to inhibit melanogenesis via the adrenergic receptors. The ADRβ3 agonists may comprise one or more compounds selected from the group consisting of ZD7114, amibegron, solabegron, L-796568, CL-316243, LY-368842, and combinations thereof.

The present inventors also identified gene targets suitable for melanogenesis inhibition by using an siRNA knockdown study of the B16 mouse melanoma cell line described above. siRNA isolates genes of interest in a melanogenesis assay to evaluate their efficacy as melanogenesis regulators. siRNA technology employs a short interfering RNA (siRNA) which is exogenously introduced into the B16 cells by transfection to inhibit the activities of an individual gene, leading to either up-regulation or down-regulation of melanogenesis in a mouse melanoma cell line (B16-F1).

Figure 6:
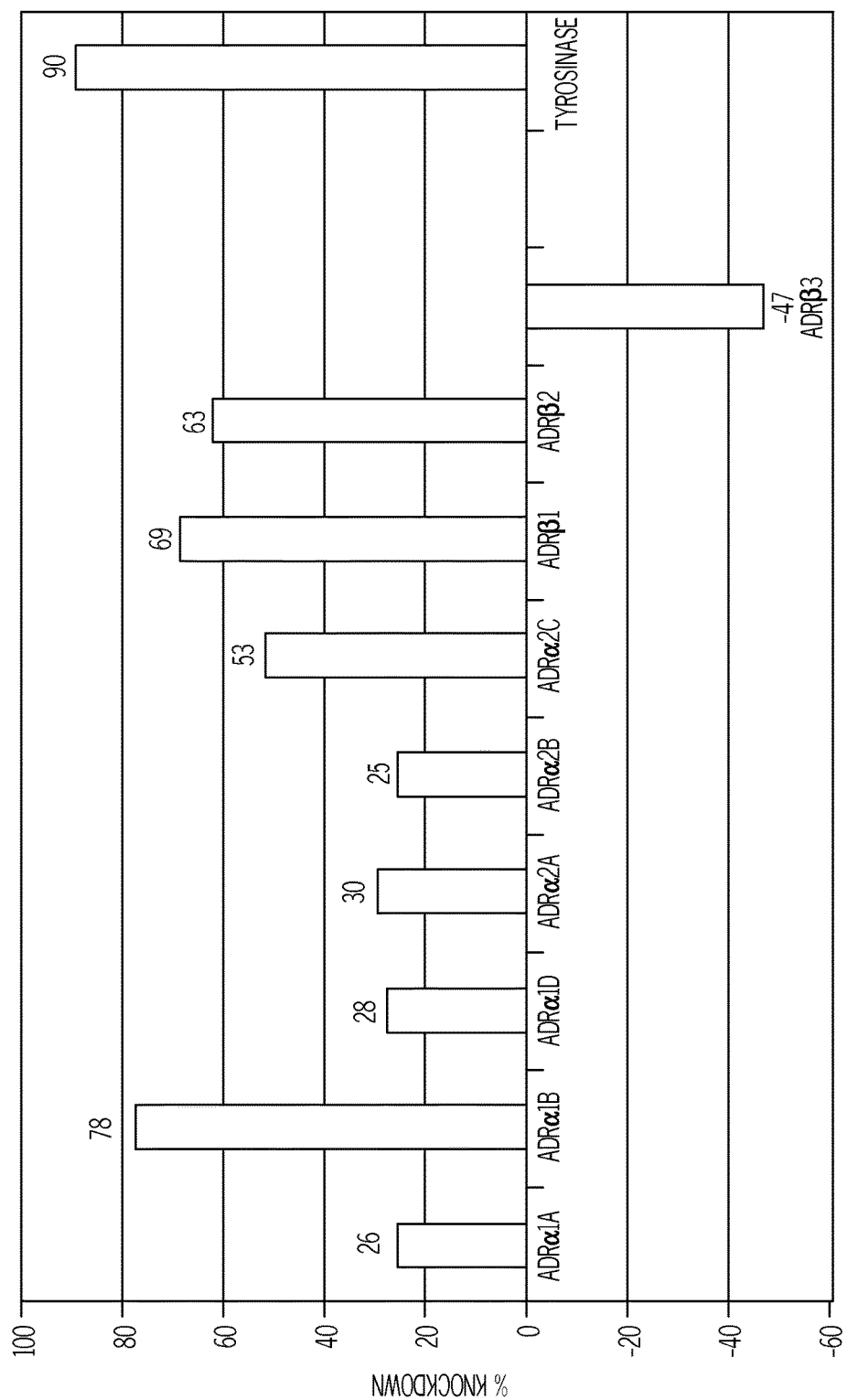
FIG. 6 is a graphical illustration of siRNA knockdown data for a B16 melanin synthesis assay, wherein adrenergic receptors are compared based on the % Knockdown metric.
Figure 7:
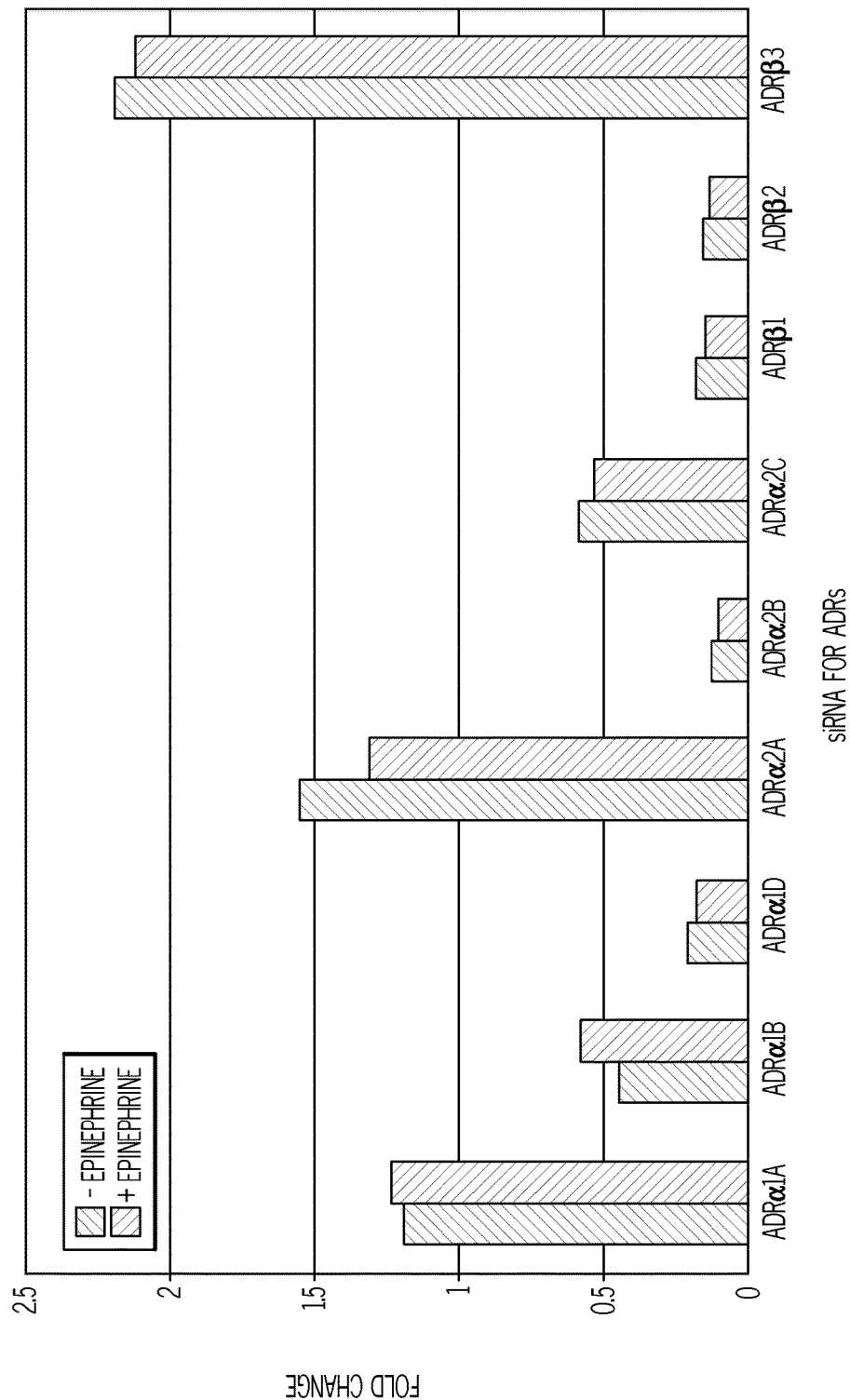
FIG. 7 is a graphical illustration of siRNA knockdown data for a B16 melanin synthesis assay, wherein adrenergic receptors are compared based on fold change in the presence of epinephrine.

Referring to FIG. 6, the siRNA knockdown data demonstrates a downregulation of the ADRβ3 gene and an upregulation of the ADRβ1 and ADRβ2 genes. Referring to FIG. 7 and Table 1 above, the siRNA inhibits gene expression for ADRβ1 and ADRβ2 genes as demonstrated by the fold change value significantly below 0.5, whereas the ADRβ3 gene was highly expressed as shown by the fold change of over 2. Since the siRNA interfered with the ADRβ1 and ADRβ2 genes, these genes were not encoded into receptors that bind with epinephrine to produce melanin, thus pigmentation decreased. Since the siRNA interfered with the ADRβ3 genes, these genes were encoded into receptors that bind with epinephrine, and thereby increase melanin production.

As stated above and as illustrated in FIG. 6, the present inventors also discovered though the siRNA knockdown data that alpha adrenergic genes ADRα1B and ADRα2C are strongly linked to melanogenesis. Similar to the ADRβ1 and ADRβ2 genes, the siRNA interfered with the ADRα1B and ADRα2C genes, thus these upregulated genes were not encoded into receptors that bind with epinephrine to produce melanin Based on these discoveries, the embodiments of the present invention are directed to gene panels comprising ADRα1B genes, ADRα2C genes, or both. Embodiments of the present invention may also include biomarker panels comprising gene products of the ADRα1B genes, the ADRα2C genes, or both.

As the antagonism of ADRα1B and ADRα2C receptors is believed to impede melanogenesis, it is beneficial to screen for antagonists of ADRα1B and ADRα2C using various screening methods familiar to one of ordinary skill in the art. In further embodiments, these antagonists of ADRα1B and/or ADRα2C may be used in various cosmetic or skin care formulations used to modulate the production of melanin in age spots. In exemplary embodiments, the ADRα1B antagonists may comprise doxazosin, prazosin, or combinations thereof, and the ADRα2C antagonists may comprise yohimbine, spiroxatrine, or combinations thereof. In further exemplary embodiments, antagonists which inhibit both alpha and beta receptors may be used, e.g., carvedilol, which defines an IC50=4 ppm, and labetalol;

In addition, further embodiments of cosmetic or skin care compositions may utilize combinations of the antagonists of alpha adrenergic receptors ADRα1B and/or ADRα2C, with the ADRβ1 antagonists or ADRβ3 agonists. Targeting multiple adrenergic receptors provides greater control of melanogenesis, especially when using a combination of agonists and antagonists.

As stated above, the agents used for modulating the adrenergic receptors and thereby modifying melanin production in age spots may be incorporated into various skin care compositions e.g., a cosmetic or cleansing composition. Various compositions and components are contemplated. The skin care composition may comprise the present adrenergic receptor antagonists and agonists in various other compositions optionally comprising thickening agents, carriers, additional skin care actives, and other additional ingredients as detailed below.

In one embodiment, the skin care composition is an oil-in-water emulsion (e.g., a silicone in water emulsion), which comprises from above 0 to about 10% by weight of the agent used for modulating melanogenesis. In alternative embodiments, the skin care composition may comprises from above 0 to about 5% , or above 0 to about 1% of the agent used for modulating melanogenesis. These agents may include ADRβ1 receptor antagonists, ADRβ3 receptor agonists, ADRα1B receptor antagonists, ADRα2C receptor antagonists, or combinations thereof.

Figure 8:
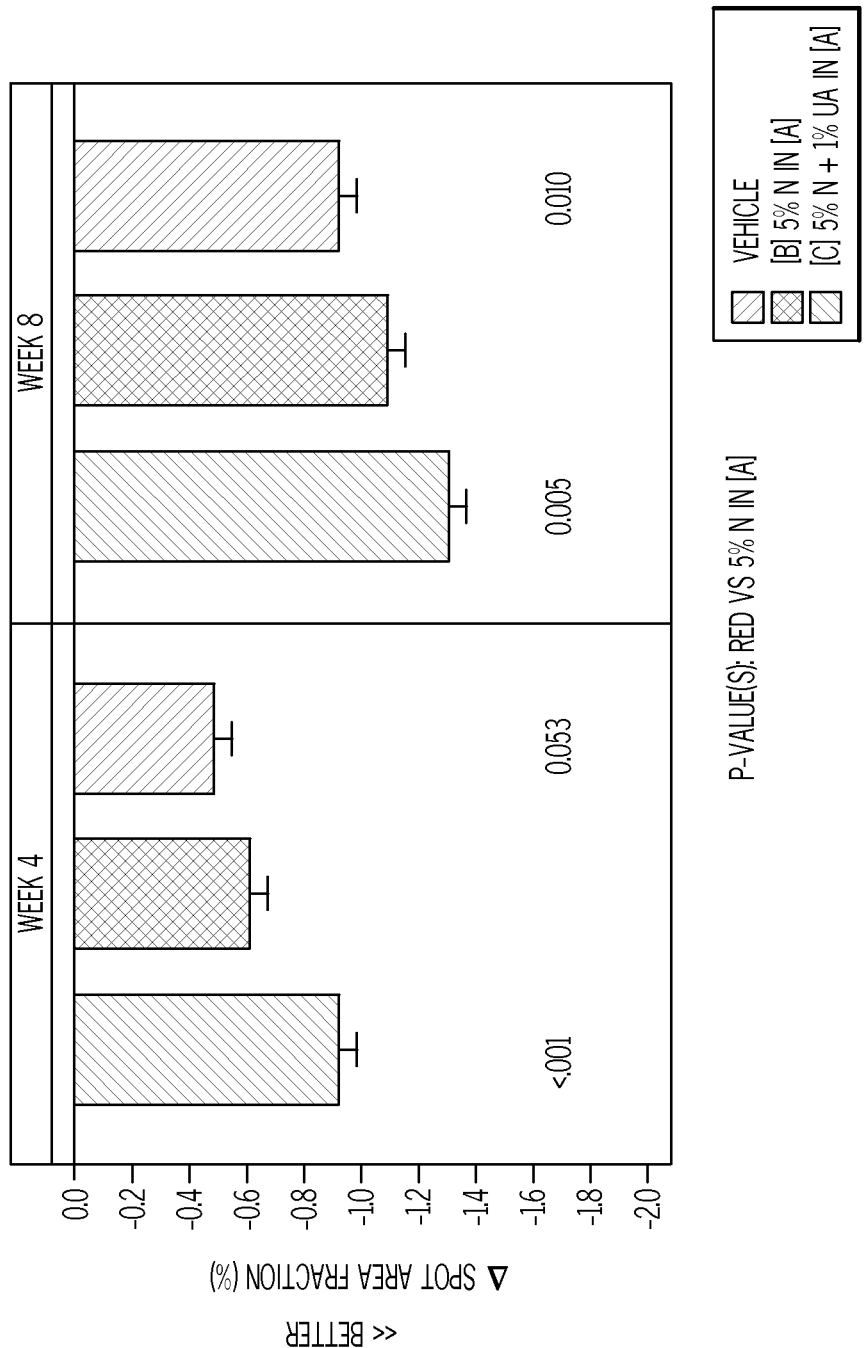
FIG. 8 is a comparative graphical illustration showing the decrease in spot fraction (%) when a human subject administers a skin care product with undecylenoyl phenylalanine (commercially available under the tradename Sepiwhite®), an ADRβ1 receptor antagonist vs. skin care products without ADRβ1 receptor inhibitors.

Referring to FIG. 8, a comparative experiment was conducted to evaluate the efficacy of a skin care composition comprising an ADRβ1 antagonist undecylenoyl phenylalanine (Sepiwhite). In the experiment, the human subjects in the study applied two of the following three products on either side of the face for a 4 or 8 week span: 1) an oil-in-water skin moisturizer (Vehicle); 2) an oil-in-water skin moisturizer containing 5% niacinamide (5% N), which is known skin lightening agent; or 3) a oil-in-water skin moisturizer containing 5% niacinamide and 1% undecylenoyl phenylalanine (5% N+1% UA). As shown in FIG. 8, the formulation with the undecylenoyl phenylalanine (ADRβ1 antagonist) demonstrated the highest decrease in spot area fraction (%), wherein the spot area fraction is the percentage of age spots area occupied in the masked area (region of interest) for image analysis for spot area quantification. As the study progressed from 4 to 8 weeks, the spot fraction (%) further decreased and demonstrated statistically significant decrease compared to the formula with niacinamide alone, thereby suggesting that long term application of skin care compositions comprising ADRβ1 antagonist would greatly minimize melanogenesis in age spots.

In addition to the exemplary oil-in-water emulsion, various additional various skin care compositions and ingredients therein are contemplated as described below. These compositions are described in Bissett et al U.S. Publication 20060074097, which is incorporated by reference herein in its entirety.

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Various regimens for applying the composition are contemplated herein. In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic applications continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are, in mg composition/$cm^2$ skin, from about 0.1 mg/$cm^2$ to about 20 mg/$cm^2$. A particularly useful application amount is about 0.5 mg/$cm^2$ to about 10 mg/$cm^2$.

Regulating keratinous tissue condition is preferably practiced by applying a composition in the form of a skin lotion, clear lotion, milky lotion, cream, gel, foam, ointment, paste, emulsion, spray, conditioner, tonic, cosmetic, lipstick, foundation, nail polish, after-shave, or the like which is intended to be left on the skin or other keratinous tissue for some esthetic, prophylactic, therapeutic or other benefit (i.e., a "leave-on" composition). After applying the composition to the keratinous tissue (e.g., skin), it is preferably left on for a period of at least about 15 minutes, more preferably at least about 30 minutes, even more preferably at least about 1 hour, most preferably for at least several hours, e.g., up to about 12 hours. Any part of the external portion of the face, hair, and/or nails can be treated, e.g., face, lips, under-eye area, eyelids, scalp, neck, torso, arms, hands, legs, fingernails, toenails, scalp hair, eyelashes, eyebrows, etc. The application of the present compositions may be done using, e.g., the palms of the hands and/or fingers, an implement, e.g., a cotton ball, swab, pad etc.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is also noted that recitations herein of "at least one" component, element, etc., should not be used to create an inference that the alternative use of the articles "a" or "an" should be limited to a single component, element, etc. It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

In the above description, genes are denoted with capital letters and italics, and proteins or receptor proteins are capitalized without italics.

All documents cited in the application are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

What is claimed is:

1. A screening method for determining whether a test agent, which is suitable for use in a topical cosmetic composition, is effective for modifying the appearance of pigmented skin, the method comprising:
   contacting a cell, a cell culture, or bulk cells with the test agent, wherein the cell, the cell culture, or the bulk cells comprise ADRβ1 receptors and wherein the test agent is a cosmetic agent; and
   determining based on the binding interaction of the test agent with the ADRβ1 receptors whether the test agent is an effective ADRβ1 receptor antagonist suitable for modifying the appearance of pigmented skin, wherein the test agent is considered to be an effective ADRβ1 receptor antagonist when it defines a half maximal inhibitory concentration of less than about 1000 ppm.

2. The screening method of claim 1 wherein the ADRβ1 receptor antagonists also act as antagonists of the ADRβ2 receptors.

3. The screening method of claim 1 further comprising contacting a second cell, a second cell culture, or a second set of bulk cells with the test agent and determining the test agent as effective for modifying the appearance of pigmented skin if the test agent is an antagonist of the ADRβ2 receptors.

4. The screening method of claim 1, further comprising evaluating the test agent in a melanin synthesis assay selected from the group consisting of a B16 cell assay or a skin model.

5. The screening method of claim 1 wherein the test agent identified as an ADRβ1 receptor antagonist defines a half maximal inhibitory concentration of less than about 100 ppm.

6. The screening method of claim 1 wherein the test agent identified as an ADRβ1 receptor antagonist defines a half maximal inhibitory concentration of less than about 50 ppm.

7. A screening method for determining at least one test agent as effective for modifying the appearance of pigmented skin, the method comprising:
   contacting a cell, a cell culture, or bulk cells with the test agent, wherein the cell, the cell culture, or the bulk cells comprise ADRβ3 receptors; and
   determining based on the binding interaction of the test agent with the ADRβ3 receptors whether the test agent is an ADRβ3 receptor agonist suitable for modifying the appearance of pigmented skin.

8. A screening method for determining at least one test agent as effective for modifying the appearance of pigmented skin, the method comprising:
   contacting a cell, a cell culture, or bulk cells with the test agent, wherein the cell, the cell culture, or the bulk cells comprise ADRα1B receptors;
   determining based on the binding interaction of the test agent with the ADRα1B receptors whether the test agent is an ADRα1B receptor antagonist suitable for modifying the appearance of pigmented skin.

9. A screening method for determining at least one test agent as effective for modifying the appearance of pigmented skin, the method comprising:
   contacting a cell, a cell culture, or bulk cells with the test agent, wherein the cell, the cell culture, or the bulk cells comprise ADRα2C receptors;
   determining based on the binding interaction of the test agent with the ADRα2C receptors whether the test agent is an ADRα2C receptor antagonist suitable for modifying the appearance of pigmented skin.

* * * * *